(12) United States Patent
Ogiso

(10) Patent No.: US 11,382,822 B2
(45) Date of Patent: Jul. 12, 2022

(54) MASSAGE DEVICE FOR SEAT

(71) Applicant: AISIN CORPORATION, Aichi (JP)

(72) Inventor: Takashi Ogiso, Tajimi (JP)

(73) Assignee: AISIN CORPORATION, Kariya (JP)

( * ) Notice: Subject to any disclaimer, the term of this patent is extended or adjusted under 35 U.S.C. 154(b) by 371 days.

(21) Appl. No.: 16/499,899

(22) PCT Filed: Mar. 13, 2018

(86) PCT No.: PCT/JP2018/009597
§ 371 (c)(1),
(2) Date: Oct. 1, 2019

(87) PCT Pub. No.: WO2018/186115
PCT Pub. Date: Oct. 11, 2018

(65) Prior Publication Data
US 2020/0113772 A1   Apr. 16, 2020

(30) Foreign Application Priority Data

Apr. 6, 2017   (JP) .............................. JP2017-075819

(51) Int. Cl.
*A61H 7/00* (2006.01)
*A47C 7/72* (2006.01)
*A61B 5/00* (2006.01)

(52) U.S. Cl.
CPC .............. *A61H 7/001* (2013.01); *A47C 7/72* (2013.01); *A61B 5/6893* (2013.01);
(Continued)

(58) Field of Classification Search
CPC ........ A47C 7/72; A61B 5/6893; B60N 2/976; A61H 7/00; A61H 7/001; A61H 15/00;
(Continued)

(56) References Cited

U.S. PATENT DOCUMENTS 6,832,991 B1 * 12/2004 Inada ................. A61H 15/0078
601/99
2005/0101890 A1 * 5/2005 Mizoguchi ............... A61H 1/00
601/84

(Continued)

FOREIGN PATENT DOCUMENTS

EP      1 145 700 A1   10/2001
JP       8-322895 A    12/1996
(Continued)

OTHER PUBLICATIONS

Extended European Search Report dated Mar. 11, 2020, in Patent Application No. 18781004.9, 8 pages.
(Continued)

*Primary Examiner* — Timothy A Stanis
*Assistant Examiner* — Matthew R Moon
(74) *Attorney, Agent, or Firm* — Oblon, McClelland, Maier & Neustadt, L.L.P.

(57) ABSTRACT

A massage device for a seat includes a pressing portion configured to expand to press a seat occupant seated on the seat, an adjustment portion configured to adjust a position of the pressing portion between the seat occupant and the seat, a deformation detector configured to detect deformation of the seat caused by expansion of the pressing portion, and a controller configured to control the adjustment portion based on a detection result of the deformation detector.

18 Claims, 13 Drawing Sheets

(52) U.S. Cl.
CPC ......... *A61H 2201/1647* (2013.01); *A61H 2201/5071* (2013.01); *A61H 2203/0431* (2013.01)

(58) Field of Classification Search
CPC ............ A61H 2205/081; A61H 23/006; A61H 23/04; A61H 2203/0431; A61H 2201/0134; A61H 2201/0138; A61H 2201/0142; A61H 2201/0146; A61H 2201/0149; A61H 2201/0157; A61H 2201/1623; A61H 2201/1647; A61H 2201/1654; A61H 2201/1678; A61H 2201/5007; A61H 2201/5071
See application file for complete search history.

(56) References Cited

U.S. PATENT DOCUMENTS

2010/0137761 A1* 6/2010 Taniguchi ............ A61H 7/00
601/112
2012/0265112 A1 10/2012 Chen
2015/0335167 A1* 11/2015 Cinquin ............ A61B 5/1115
5/655.3
2018/0037236 A1 2/2018 Yamaguchi
2018/0257534 A1* 9/2018 Mizoi ................ A47C 7/425

FOREIGN PATENT DOCUMENTS

| JP | 2005-259 A | 1/2005 | |
| JP | 2013-215402 A | 10/2013 | |
| JP | 2015-19891 A | 2/2015 | |
| JP | 2015-33651 A | 2/2015 | |
| WO | WO-2007009274 A2 * | 1/2007 | ............ B60N 2/99 |

OTHER PUBLICATIONS

International Search Report dated May 1, 2018 in PCT/JP2018/009597 filed Mar. 13, 2018.

* cited by examiner

MASSAGE DEVICE FOR SEAT

TECHNICAL FIELD

The present invention relates to a massage device for a seat.

BACKGROUND ART

Conventionally, massage devices that massage a seat occupant seated in a seat have been known. Patent Document 1 discloses an example of a massage device that includes a chair body (seat), airbags (pressing portions) incorporated in the chair body, and a control means for controlling intake and discharge of air to and from the airbags.

PRIOR ART DOCUMENT

Patent Document

Patent Document 1: Japanese Laid-Open Patent Publication No. 2013-215402

SUMMARY OF THE INVENTION

Problems that the Invention is to Solve

In the above-described massage device, during expansion of the airbags, the chair body may be pressed and deformed. This may attenuate the force of the airbags that presses the seat occupant.

An objective of the present invention is to provide a massage device for a seat that limits the attenuation of a force of a pressing portion that presses a seat occupant.

Means for Solving the Problem

A massage device for a seat that solves the above-described problem includes a pressing portion configured to expand to press a seat occupant seated on the seat, an adjustment portion configured to adjust a position of the pressing portion between the seat occupant and the seat, a deformation detector configured to detect deformation of the seat caused by expansion of the pressing portion, and a controller configured to control the adjustment portion based on a detection result of the deformation detector.

MODES FOR CARRYING OUT THE INVENTION

A massage device for a seat according to an embodiment will now be described with reference to the drawings.

Figure 1:
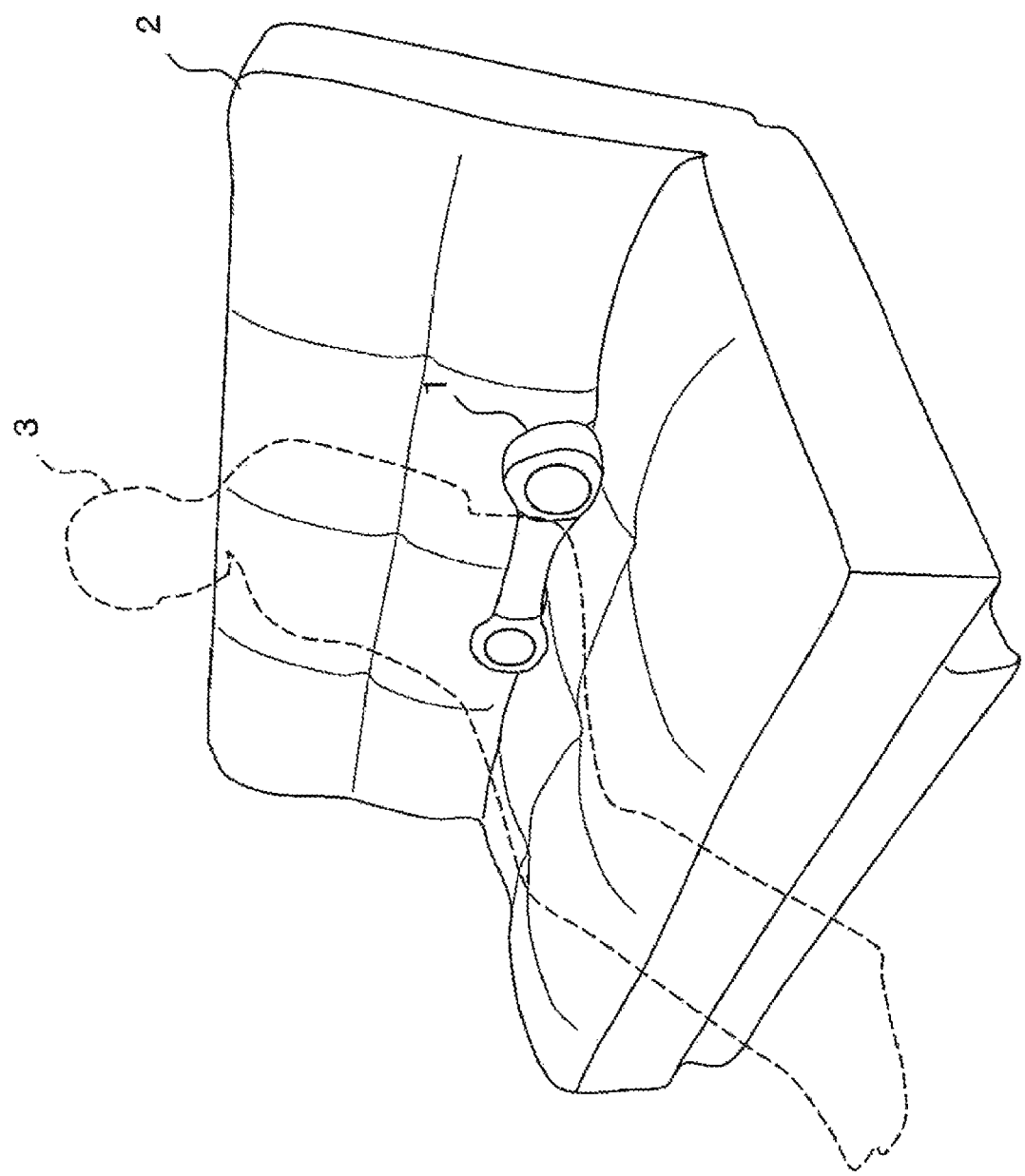
FIG. 1 is a perspective view showing a usage of a massage device for a seat according to an embodiment.

As shown in FIG. 1, a massage device 1 for a seat (hereinafter simply referred to as "massage device") is arranged on a seat 2, on which a seat occupant 3 is seated. The massage device 1 is separate from the seat 2. Further, it is preferred that the massage device 1 be covered with a cover. The seat 2 may be, for example, a sofa or a chair. Alternatively, the seat 2 may be a seat arranged in a vehicle or the like.

Figure 2:
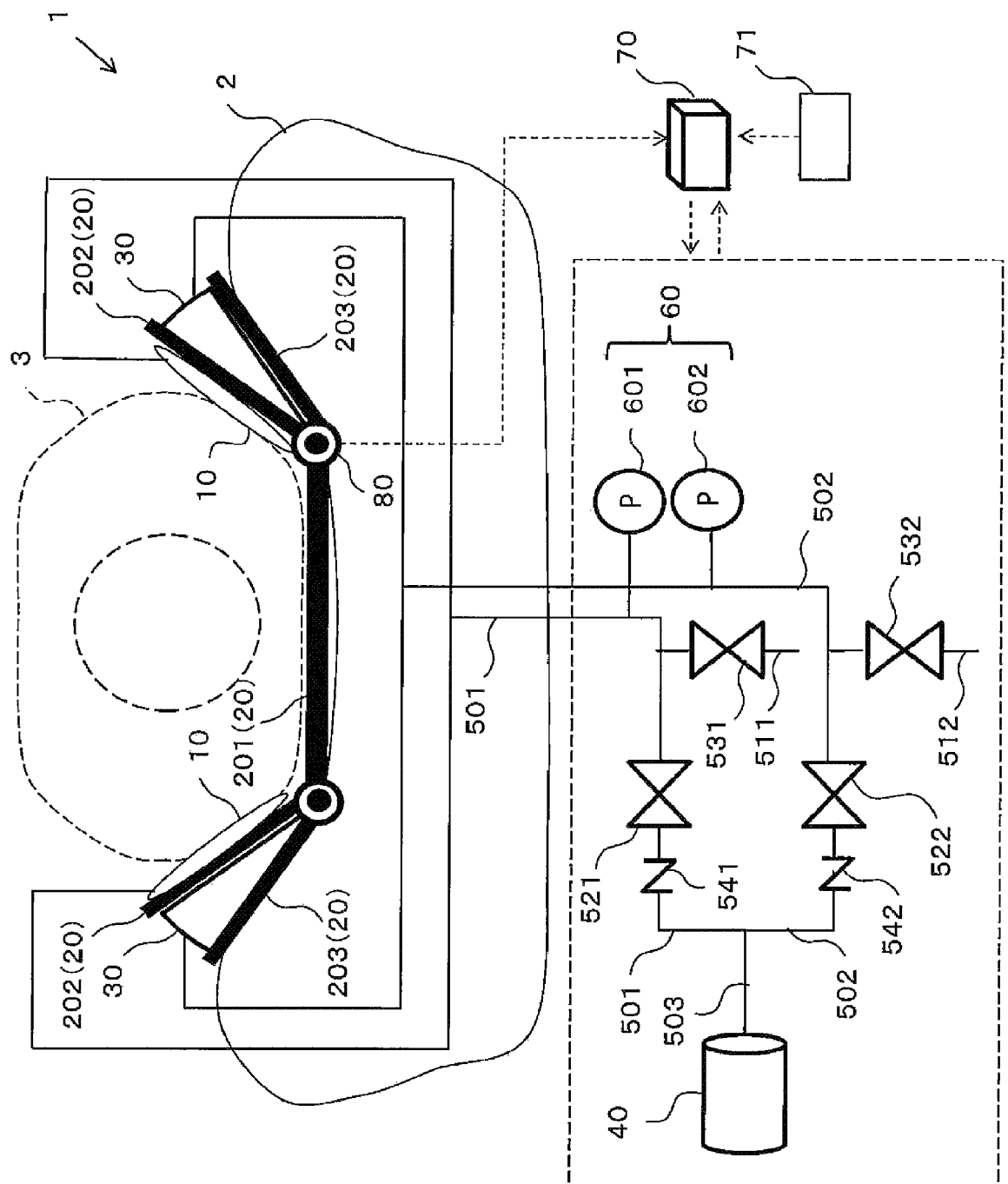
FIG. 2 is a diagram showing the massage device of FIG. 1.

As shown in FIG. 2, the massage device 1 includes two pressing portions 10, which massage the seat occupant 3, supports 20, which support the pressing portions 10, two adjustment portions 30, which respectively adjust the positions of the pressing portions 10, an angle detector 80 (deformation detector), which adjusts the position of one of the pressing portions 10, a compressor 40 (fluid supply source), which supplies the pressing portions 10 and the adjustment portions 30 with compressed air, a pressure detector 60, which detects the inner pressure of the pressing portion 10 and the adjustment portion 30, and a controller 70, which controls the driving of the compressor 40.

Further, the massage device 1 includes a first passage 501, which is connected to the two pressing portions 10, a second passage 502, which is connected to the two adjustment portions 30, and a third passage 503, which is connected to the compressor 40. The first passage 501 and the second passage 502 are connected to the third passage 503 and extended such that the first passage 501 and the second passage 502 branch from the third passage 503 from each other.

As shown in FIG. 2, the pressing portions 10 are arranged in contact with the seat occupant 3. The pressing portions 10 are made of elastic materials. Further, the pressing portions 10 are bag-shaped members, i.e., airbags. Thus, the pressing portions 10 expand when air is supplied and contract when air is discharged. When the pressing portions 10 expand, the pressing portions 10 press the seat occupant 3.

The supports 20 include a first support 201, which is in contact with the back surface of the seat occupant 3, two second supports 202, which respectively support the pressing portions 10, and two third supports 203, which are in contact with the seat 2 at positions that respectively correspond to the adjustment portions 30. Each of the first support 201, the second supports 202, and the third supports 203 is a substantially rectangular plate-shaped member. The pressing portions 10 are arranged one by one on the opposite sides of the first support 201 in the longitudinal direction, and the adjustment portions 30 are arranged one by one on the opposite sides of the first support 201 in the longitudinal direction.

The second supports 202 are coupled one by one to the opposite ends of the first support 201 in the longitudinal direction, and the third supports 203 are coupled one by one to the opposite ends of the first support 201 in the longitudinal direction. Each of the second supports 202 and the third supports 203 is pivotally coupled to the corresponding end of the first support 201. Each of the second supports 202 and the third supports 203 pivots about a pivotal axis extending in the lateral direction of the first support 201, which is orthogonal to the longitudinal direction. Further, the massage device 1 is arranged on the seat 2 such that the second supports 202 are located between the third supports 203 and the seat occupant 3.

The pressing portions 10 are attached to parts of the second supports 202 facing the seat occupant 3. Further, the adjustment portions 30 are arranged between the second supports 202 and the third supports 203. That is, the adjustment portions 30 are arranged between the pressing portions 10 and the seat 2. The pressing portions 10 are supported by the adjustment portions 30 with the second supports 202 located in between.

The adjustment portions 30 are supported by the second supports 202 and the third supports 203, which are arranged such that the adjustment portions 30 are located between the second supports 202 and the third supports 203. In the same manner as the pressing portions 10, the adjustment portions 30 are bag-shaped members made of elastic materials, that is, airbags. The adjustment portions 30 expand in a sectoral manner from the parts of the second and third supports 202 and 203 that are coupled to the first support 201. Thus, when the adjustment portions 30 expand, the adjustment portions 30 cause the second supports 202 to pivot toward the seat occupant 3. That is, the adjustment portions 30 adjust the positions of the pressing portions 10 between the seat occupant 3 and the seat 2.

The angle detector 80 is arranged on the part where the first support 201 and one of the second supports 202 are coupled to each other, that is, one side of the first support 201 in the longitudinal direction. The angle detector 80 detects an angle formed by the second support 202 and the first support 201. The angle formed by the second support 202 and the first support 201 is an angle formed on a side on which the pressing portion 10 is arranged relative to the second support 202. Since the second support 202 is arranged between the pressing portion 10 and the adjustment portion 30, the angle detector 80 can detect the position of the part of the pressing portion 10 facing the adjustment portion 30. In other words, the angle detector 80 detects the position of a part of the pressing portion 10 supported by the adjustment portion 30 (more specifically, a part supported by the second support 202). The part of the pressing portion 10 facing the adjustment portion 30 (the part supported by the adjustment portion 30) is referred to as a "supported part" of the pressing portion 10. The angle detector 80 simply needs to be an angular sensor that changes an output voltage in accordance with, for example, a rotational angle.

The first passage 501, the second passage 502, and the third passage 503 may be formed by, for example, elastic tubes or metal pipes. In the following description, a side of the first passage 501, the second passage 502, and the third passage 503 that is proximate to the compressor 40, which is a supply source of air, is referred to an "upstream side," and a side distant from the compressor 40 is referred to as a "downstream side."

The first passage 501 includes a first branch passage 511, which branches from the first passage 501. The first branch passage 511 has a first end, which is connected to the first passage 501, and a second end, which is opened to the atmosphere. Further, the second passage 502 includes a second branch passage 512, which branches from the second passage 502. The second branch passage 512 has a first end, which is connected to the second passage 502, and a second end, which is opened to the atmosphere.

The first passage 501 includes a first switch valve 521, and the second passage 502 includes a second switch valve 522. The first branch passage 511 includes a first discharge valve 531, and the second branch passage 512 includes a second discharge valve 532. The first switch valve 521, the second switch valve 522, the first discharge valve 531, and the second discharge valve 532 are solenoid valves electrically switched to an open state or a closed state.

The first switch valve 521 is located upstream of a part where the first passage 501 and the first branch passage 511 are connected to each other in the first passage 501. Further, the second switch valve 522 is located upstream of a part where the second passage 502 and the second branch passage 512 are connected to each other in the second passage 502.

The first switch valve 521, the second switch valve 522, the first discharge valve 531, and the second discharge valve 532 are selectively switched to the open state, which allows air to flow in the passages where the valves are arranged, and the closed state, which restricts the flow of air in the passages where the valves are arranged.

In addition, the first passage 501 includes a first check valve 541, and the second passage 502 includes a second check valve 542. The first check valve 541 is located upstream of the first switch valve 521. The second check valve 542 is located upstream of the second switch valve 522. The first check valve 541 allows the flow of air from the compressor 40 toward the pressing portions 10 and restricts the flow of air from the pressing portions 10 toward the compressor 40. Further, the second check valve 542 allows the flow of air from the compressor 40 toward the adjustment portions 30 and restricts the flow of air from the adjustment portions 30 toward the compressor 40.

The pressure detector 60 includes a first pressure detector 601, which detects the inner pressure of the first passage 501, and a second pressure detector 602, which detects the inner pressure of the second passage 502. The pressure detector 60 simply needs to be, for example, a pressure sensor that measures the pressure of fluid with a pressure sensitive element and converts the measured pressure into an electrical signal. The first pressure detector 601 is located downstream of the first switch valve 521 in the first passage 501. The inner pressure of the first passage 501 is the same at any locations between the first switch valve 521 and the pressing portions 10. Thus, the first pressure detector 601 detects the inner pressure of the pressing portions 10. In addition, the second pressure detector 602 is located downstream of the second switch valve 522 in the second passage 502. The inner pressure of the second passage 502 is the same at any locations between the second switch valve 522 and the adjustment portions 30. Thus, the second pressure detector 602 detects the inner pressure of the adjustment portions 30.

The controller 70 is electrically connected to the angle detector 80, the compressor 40, the first switch valve 521, the second switch valve 522, the first discharge valve 531, the second switch valve 522, and the pressure detector 60. The controller 70 is configured by a known microcomputer including a CPU, a RAM, a ROM, and the like. By using the CPU to execute the programs read from the ROM, the controller 70 determines information obtained from the angle detector 80 and the pressure detector 60 and controls driving of the compressor 40, the first switch valve 521, the second switch valve 522, the first discharge valve 531, and the second discharge valve 532. When receiving a signal from an operation portion 71, which includes a switch electrically connected to the controller 70, the compressor 40 simply needs to start driving the compressor 40, the first switch valve 521, the second switch valve 522, the first discharge valve 531, and the second discharge valve 532.

The contents of control performed by the massage device 1 will now be described.

Figure 3:
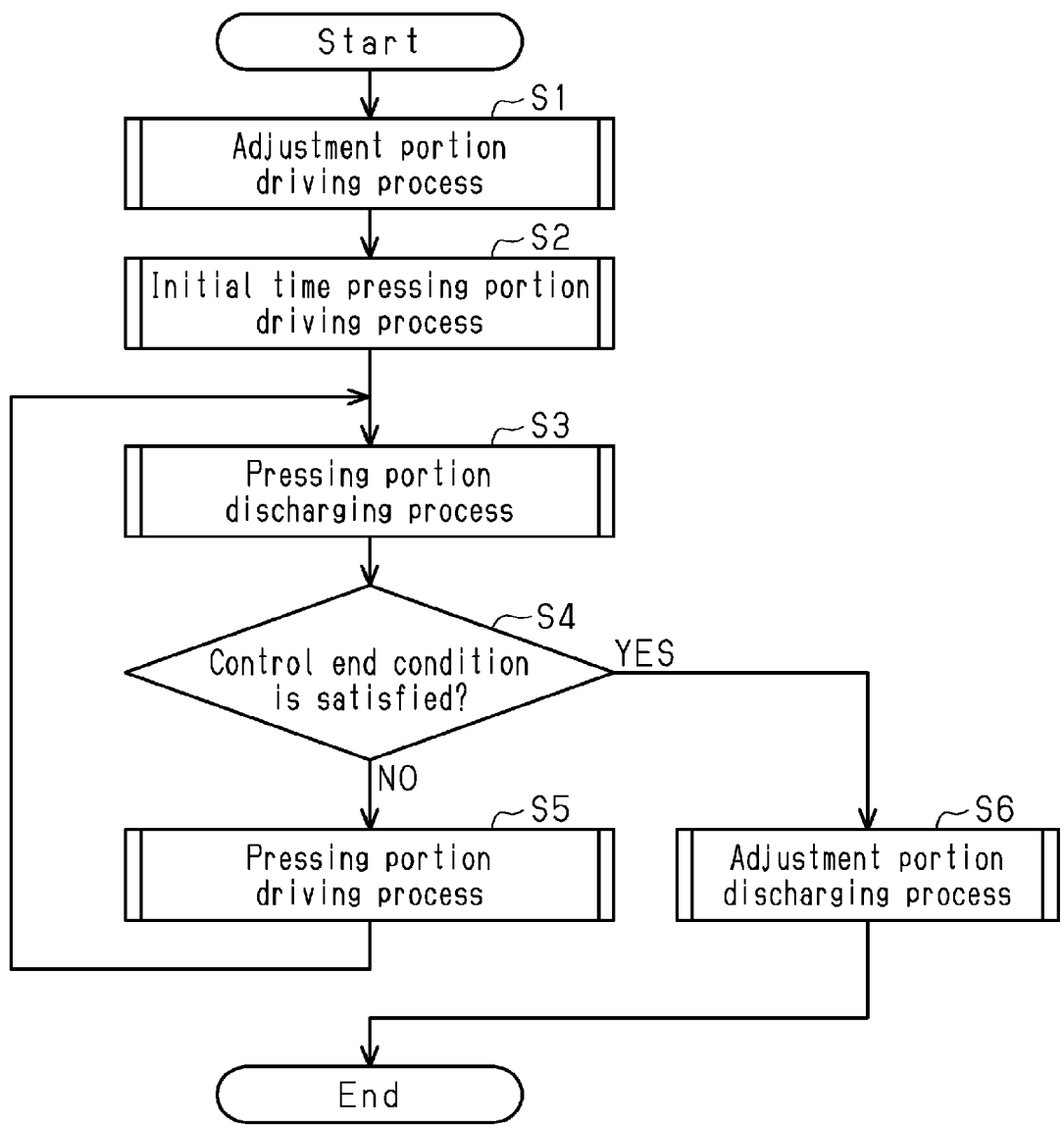
FIG. 3 is a flowchart of a process executed when the controller of the massage device shown in FIG. 2 massages a seat occupant.

The controller 70 executes a process for massaging the seat occupant 3 illustrated in FIG. 3. The processes of FIGS. 4 to 8 are the subroutines of the process of FIG. 3.

First, the process of massaging the seat occupant 3 will now be described with reference to the flowchart of FIG. 3. This process is started when the seat occupant 3 operates an operation switch arranged on the operation portion 71. Before the process of FIG. 3 starts, the pressing portion 10 and the adjustment portion 30 are contracted, the compressor 40 is stopped, and the first switch valve 521, the second switch valve 522, the first discharge valve 531, and the second discharge valve 532 are closed.

In step S1, the controller 70 executes an adjustment portion driving process. That is, the controller 70 causes the adjustment portions 30 to expand so that the pressing portion 10 contacts the seat occupant 3. In the following description, causing the adjustment portions 30 to expand or contract is also referred to as "driving the adjustment portions 30." The detailed contents of the process will be described in the process of FIG. 4 (described later). Upon completion of the process of step S1, the controller 70 proceeds to step S2.

In step S2, the controller 70 executes an initial time pressing portion driving process. That is, the controller 70 causes the pressing portion 10 to expand so that the pressing portion 10 presses the seat occupant 3. Further, when the seat 2 deforms during expansion of the pressing portion 10, the controller 70 drives the adjustment portion 30. The detailed contents of the process will be described in the process of FIG. 5 (described later). Upon completion of the process of step S2, the controller 70 proceeds to step S3.

In step S3, the controller 70 executes a pressing portion discharging process. That is, the controller 70 causes air in the pressing portions 10 to be discharged. The detailed contents of this process will be described in the process of FIG. 6 (described later). Upon completion of the process of step S3, the controller 70 proceeds to step S4.

In step S4, the controller 70 determines whether a control end condition is satisfied. For example, the "control end condition" may mean that several tens of seconds to several minutes has passed since the operation switch of the operation portion 71 was operated. Alternatively, the control end condition may mean that the operation switch has been operated for ending. When the control end condition is not satisfied (step S4: No), the controller 70 proceeds to step S5. When the control end condition is satisfied (step S4: Yes), the controller 70 proceeds to step S6.

In step S5, the controller 70 executes a pressing portion driving process. That is, the controller 70 causes the pressing portion 10 to expand and press the seat occupant 3. The detailed contents of the process will be described in the process of FIG. 7 (described later). Upon completion of the process of step S5, the controller 70 returns to step S3.

In step S6, the controller 70 executes an adjustment portion discharging process. That is, the controller 70 causes air in the adjustment portion 30 to be discharged. The detailed contents of the process will be described in the process of FIG. 8 (described later). Upon completion of the process of step S6, the controller 70 temporarily ends the current process.

The adjustment portion driving process will now be described with reference to the flowchart of FIG. 4. In this process, the controller 70 drives the adjustment portion 30 to cause the pressing portion 10 to contact the seat occupant 3.

In step S11, the controller 70 causes the compressor 40 to be driven. Subsequently, in step S12, the controller 70 opens the second switch valve 522. In this manner, the controller 70 supplies compressed air from the compressor 40 to the adjustment portion 30 to expand the adjustment portion 30. Upon completion of the process of step S12, the controller 70 proceeds to step S13.

In step S13, the controller 70 determines whether the gradient of the inner pressure of the adjustment portion 30 is greater than or equal to a first threshold value. The gradient of the inner pressure of the adjustment portion 30 is the amount of change in the inner pressure of the adjustment portion 30 per unit of time, that is, a temporal change rate of the inner pressure of the adjustment portion 30. Further, the inner pressure of the adjustment portion 30 can be obtained from the detection result of the second pressure detector 602.

When the pressing portion 10 contacts the seat occupant 3 during expansion of the adjustment portion 30, the inner pressure of the adjustment portion 30 easily increases. That is, when the gradient of the inner pressure of the adjustment portion 30 until the pressing portion 10 contacts the seat occupant 3 is referred to as a first gradient and the gradient of the inner pressure of the adjustment portion 30 after the pressing portion 10 contacts the seat occupant 3 is referred to as a second gradient, the second gradient is larger than the first gradient. Thus, when the first threshold value is set to be larger than the first gradient and smaller than the second gradient, the controller 70 can determine whether the pressing portion 10 is in contact with the seat occupant 3.

When the gradient of the inner pressure of the adjustment portion 30 is greater than or equal to the first threshold value (step S13: Yes), the controller 70 proceeds to step S14. When the gradient of the inner pressure of the adjustment portion 30 is less than the first threshold value (step S13: No), the controller 70 returns to step S13. Thus, the process of step S13 is also referred to as a process of causing the adjustment portion 30 to expand until the pressing portion 10 contacts the seat occupant 3.

In step S14, the controller 70 closes the second switch valve 522. In this manner, the controller 70 restricts the supply of compressed air from the compressor 40 to the adjustment portion 30 so that the adjustment portion 30 stops expanding. Upon completion of the process of step S14, the controller 70 proceeds to step S15.

In step S15, the controller 70 stores the detection result (angle) of the angle detector 80. The stored value of the detection result of the angle detector 80 stored by the controller 70 is hereinafter referred to as a "stored value V." Upon completion of the process of step S15, the controller 70 temporarily ends the current process.

Figure 5:
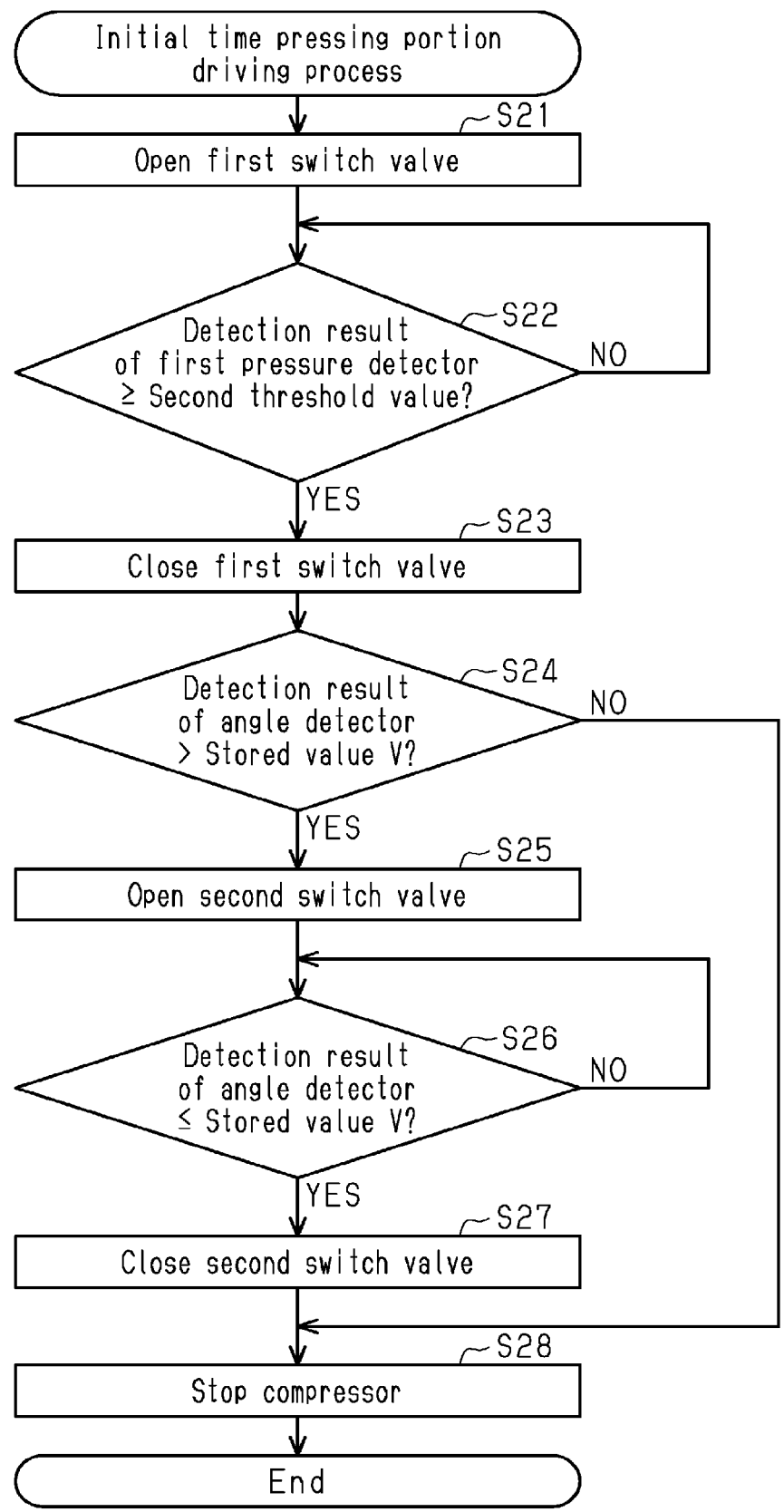
FIG. 5 is a flowchart of an initial time pressing portion driving process executed by the controller of the massage device shown in FIG. 2.

The initial time pressing portion driving process will now be described with reference to the flowchart in FIG. 5. In this process, the controller 70 causes the pressing portion 10 to expand to press the seat occupant 3. In the following description, causing the pressing portion 10 to expand or contract is also referred to as "driving the pressing portion 10." Further, when the seat 2 deforms during expansion of the pressing portion 10, the controller 70 drives the adjustment portion 30.

In step S21, the controller 70 opens the first switch valve 521. Since the compressor 40 is driven, compressed air is supplied from the compressor 40 to the pressing portion 10, thereby expanding the pressing portion 10. Upon completion of the process of step S21, the controller 70 proceeds to step S22.

In step S22, the controller 70 determines whether the detection result (pressure) of the first pressure detector 601 is greater than or equal to a second threshold value.

In a case in which the seat occupant 3 is pressed (massaged) by the pressing portion 10, the larger the amount of air supplied to the pressing portion 10 becomes, the more greatly the pressing portion 10 expands and the more strongly the seat occupant 3 is pressed. That is, the second threshold value is a threshold value for setting an upper limit of the pressure of the pressing portion 10 when the seat occupant 3 is massaged. Thus, it is preferred that the second threshold value be variably set in accordance with the strength of massage desired by the seat occupant 3.

When the detection result of the first pressure detector 601 is greater than or equal to the second threshold value (step S22: Yes), the controller 70 proceeds to step S23. When the detection result of the first pressure detector 601 is less than the second threshold value (step S22: No), the controller 70 returns to step S22.

In step S23, the controller 70 closes the first switch valve 521. In this manner, the controller 70 restricts the supply of compressed air from the compressor 40 to the pressing portion 10 so that the pressing portion 10 stops expanding. Upon completion of the process of step S23, the controller 70 proceeds to step S24.

In step S24, the controller 70 determines whether the detection result (angle) of the angle detector 80 is larger than the stored value V. That is, the controller 70 determines whether the seat 2 has been deformed by the expansion of the pressing portion 10.

When the adjustment portion 30 is not driven, the angle formed by the second support 202 and the third support 203 is constant. Thus, the change amount of the angle formed by the first support 201 and the second support 202 is equal to the change amount of the angle formed by the first support 201 and the third support 203. Further, deformation of the seat 2 changes the angle formed by the first support 201 and the third support 203. Thus, the deformation of the seat 2 caused by the expansion of the pressing portion 10 can be detected by comparing the stored value V with the detection result of the angle detector 80.

When the detection result of the angle detector 80 is larger than the stored value V (step S24: Yes), the controller 70 proceeds to step S25. When the detection result of the angle detector 80 is less than or equal to the stored value V (step S24: No), the controller 70 proceeds to step S28. The affirmative determination in step S24 indicates that the position of the second support 202 (i.e., the position of the supported part of the pressing portion 10) has moved toward the seat 2 when the first switch valve 521 is open, that is, while the pressing portion 10 is expanding.

In step S25, the controller 70 opens the second switch valve 522. In this manner, the controller 70 supplies compressed air from the compressor 40 to the adjustment portion 30 to expand the adjustment portion 30. Upon completion of the process of step S25, the controller 70 proceeds to step S26.

In step S26, the controller 70 determines whether the detection result of the angle detector 80 is less than or equal to the stored value V. When the detection result of the angle detector 80 is less than or equal to the stored value V (step S26: Yes), the controller 70 proceeds to step S27. When the detection result of the angle detector 80 is larger than the stored value V (step S26: No), the controller 70 proceeds to step S26.

In step S27, the controller 70 closes the second switch valve 522. In this manner, the controller 70 restricts the supply of compressed air from the compressor 40 to the adjustment portions 30 so that the adjustment portion 30 stops expanding. Thus, in a case in which the detection result of the angle detector 80, that is, the position of the supported part, which is the part of the pressing portion 10 facing the adjustment portion 30 (i.e., the part supported by the adjustment portion 30), changes when the pressing portion 10 is expanded from a contracted state through the processes of steps S24 to S27, the controller 70 causes the adjustment portion 30 to be driven such that the position of the supported part of the pressing portion 10 becomes a position prior to the expansion. Upon completion of the process of step S27, the controller 70 proceeds to step S28.

In step S28, the controller 70 causes the compressor 40 to stop driving. The controller 70 temporarily ends the current process.

Figure 6:
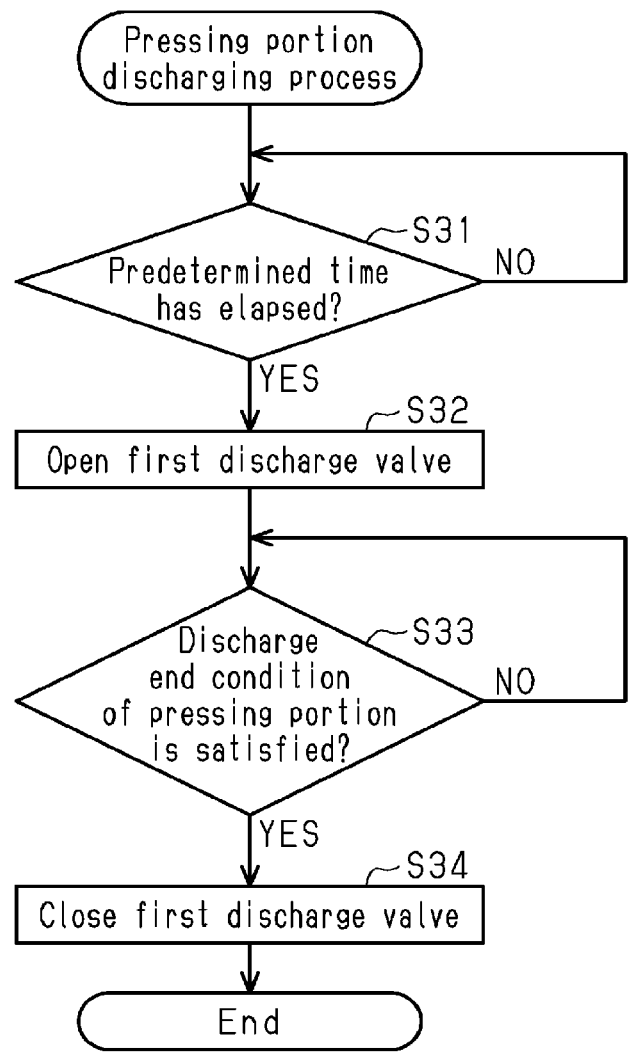
FIG. 6 is a flowchart of a pressing portion discharging process executed by the controller of the massage device shown in FIG. 2.

The pressing portion discharging process will now be described with reference to the flowchart in FIG. 6. In this process, the controller 70 causes the pressing portion 10 to contract.

In step S31, the controller 70 determines whether a predetermined time has elapsed from the beginning of the process. The "predetermined time" may refer to a predetermined fixed value or a variable value that can be changed by the seat occupant 3. When the predetermined time is a fixed value, the fixed value should be, for example, three seconds to five seconds. In this manner, the controller 70 keeps the pressing portion 10 expanded for the predetermined time so that the seat occupant 3 can feel as if he or she is pressed by the pressing portion 10. When the predetermined time has elapsed from the beginning of the current process (step S31: Yes), the controller 70 proceeds to step S32. When the predetermined time has not elapsed from the beginning of the current process (step S31: No), the controller 70 returns to step S31.

In step S32, the controller 70 opens the first discharge valve 531. In this manner, the controller 70 discharges air in the pressing portion 10 from the first branch passage 511 to contract the pressing portion 10. Upon completion of the process of step S32, the controller 70 proceeds to step S33.

In step S33, the controller 70 determines whether a discharge end condition of the pressing portion 10 is satisfied. For example, the "discharge end condition of the pressing portion 10" simply needs to be, for example, that five seconds to ten seconds has elapsed since the first discharge valve 531 was opened in step S32. In this manner, the controller 70 causes the discharge of the pressing portion 10 to continue for a sufficient amount of time. When the pressing portion 10 is contracted from an expanded state, the position of the supported part of the pressing portion 10 may be changed. In this case, the adjustment portion 30 is not driven. When the discharge end condition of the pressing portion 10 is satisfied (step S33: Yes), the controller 70 proceeds to step S34. When the discharge end condition of the pressing portion 10 is not satisfied (step S33: No), the controller 70 returns to step S33.

In step S34, the controller 70 closes the first discharge valve 531. In this manner, the controller 70 restricts the supply of air from the pressing portion 10 to the first branch passage 511 so that the pressing portion 10 stops contracting. Upon completion of the process of step S34, the controller 70 temporarily ends the current process.

Figure 7:
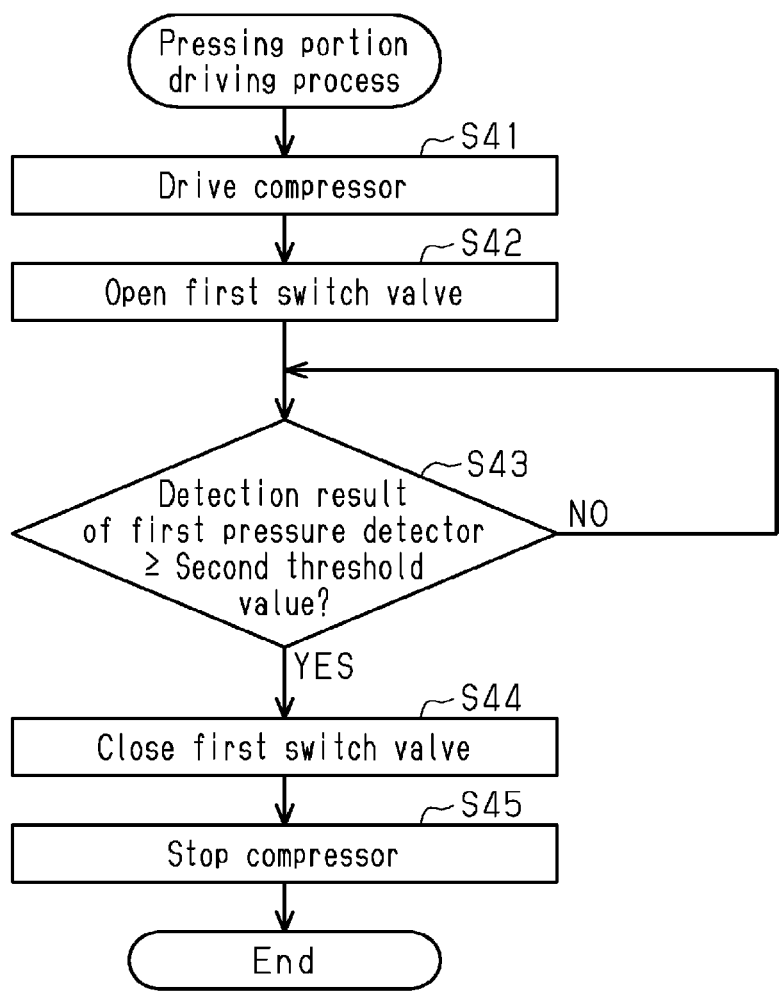
FIG. 7 is a flowchart of a pressing portion driving process executed by the controller of the massage device shown in FIG. 2.

The pressing portion driving process will now be described with reference to the flowchart in FIG. 7. In this process, the controller 70 causes the pressing portion 10 to expand to press the seat occupant 3.

In step S41, the controller 70 causes the compressor 40 to be driven. Subsequently, in step S42, the controller 70 opens the first switch valve 521. In this manner, the controller 70 supplies compressed air from the compressor 40 to the pressing portion 10 so that the pressing portion 10 expands. Upon completion of the process of step S42, the controller 70 proceeds to step S43.

In step S43, the controller 70 determines whether the detection result (pressure) of the first pressure detector 601 is greater than or equal to the second threshold value. Thus, in the same manner as step S22 of FIG. 5, the controller 70 causes the pressing portion 10 to expand until the force of pressing the seat occupant 3 with the pressing portion 10 becomes proper. When the pressing portion 10 is expanded, the position of the supported part of the pressing portion 10 may be changed. In this case, the adjustment portion 30 is not driven. When the detection result of the first pressure detector 601 is greater than or equal to the second threshold value (step S43: Yes), the controller 70 proceeds to step S44. When the detection result of the first pressure detector 601 is less than the second threshold value (step S43: No), the controller 70 returns to step S43.

In step S44, the controller 70 closes the first switch valve 521. In this manner, the controller 70 restricts the supply of compressed air from the compressor 40 to the pressing portion 10 so that the pressing portion 10 stops expanding. In step S45, the controller 70 causes the compressor 40 to stop driving, thereby temporarily ending the current process.

Figure 8:
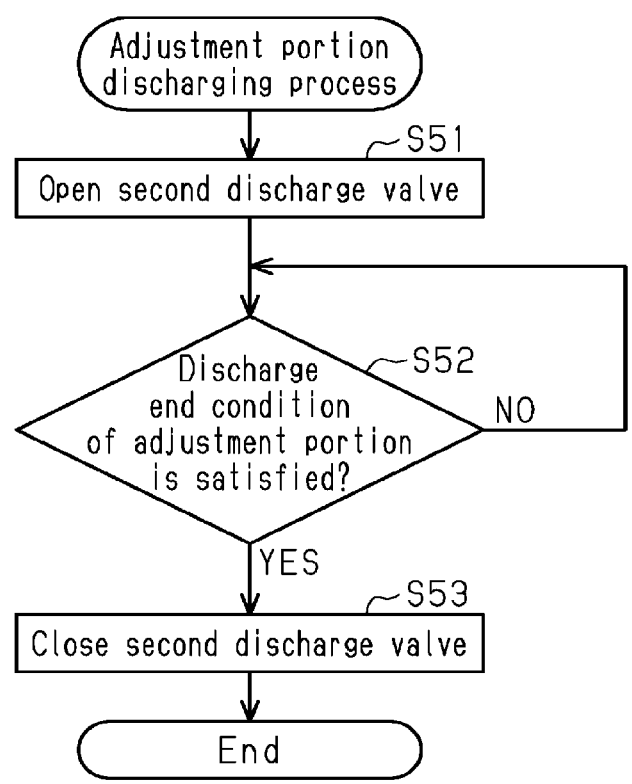
FIG. 8 is a flowchart of an adjustment portion discharging process executed by the controller of the massage device shown in FIG. 2.

Finally, the adjustment portion discharging process will be described with reference to the flowchart in FIG. 8. In this process, the controller 70 causes the adjustment portion 30 to contract.

In step S51, the controller 70 opens the second discharge valve 532. In this manner, the controller 70 discharges air in the adjustment portion 30 from the second branch passage 512 so that the adjustment portion 30 contracts. Upon completion of the process of step S51, the controller 70 proceeds to step S52.

In step S52, the controller 70 determines whether a discharge end condition of the adjustment portion 30 is satisfied. For example, the "discharge end condition of the adjustment portion 30" simply needs to be, for example, that several seconds has elapsed since the second discharge valve 532 was opened in step S51. In this manner, the controller 70 causes the discharge of the adjustment portion 30 to continue for a sufficient amount of time. When the discharge end condition of the adjustment portion 30 is satisfied (step S52: Yes), the controller 70 proceeds to step S53. When the discharge end condition of the adjustment portion 30 is not satisfied (step S52: No), the controller 70 returns to step S52.

In step S53, the controller 70 closes the second discharge valve 532. In this manner, the controller 70 restricts the discharge of air from the adjustment portion 30 to the second branch passage 512 so that the adjustment portion 30 stops contracting. Upon completion of the process of step S53, the controller 70 temporarily ends the current process.

Figure 9:
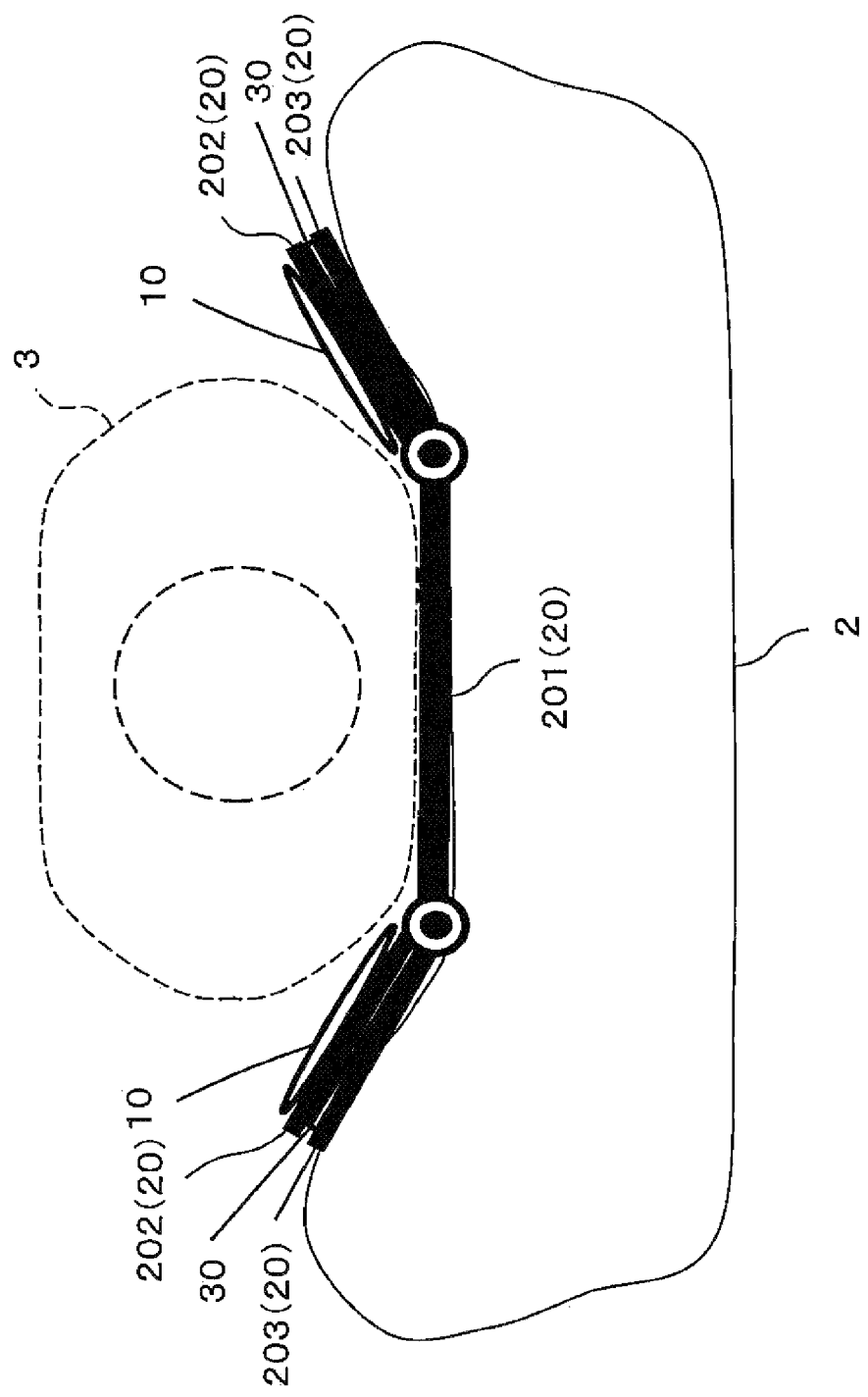
FIG. 9 is a plan view showing the pressing portions and the adjustment portions prior to being driven in the massage device of FIG. 2.

The operation of the massage device 1 will now be described. FIG. 9 shows an initial state in which the pressing portions 10 and the adjustment portions 30 are contracted.

As shown in FIG. 9, the massage device 1 is arranged on the seat 2. In this state, the first support 201 and the third supports 203 are in contact with the backrest of the seat 2. Then, the massage device 1 receives a signal from the operation portion 71 to start massaging the seat occupant 3.

Figure 10:
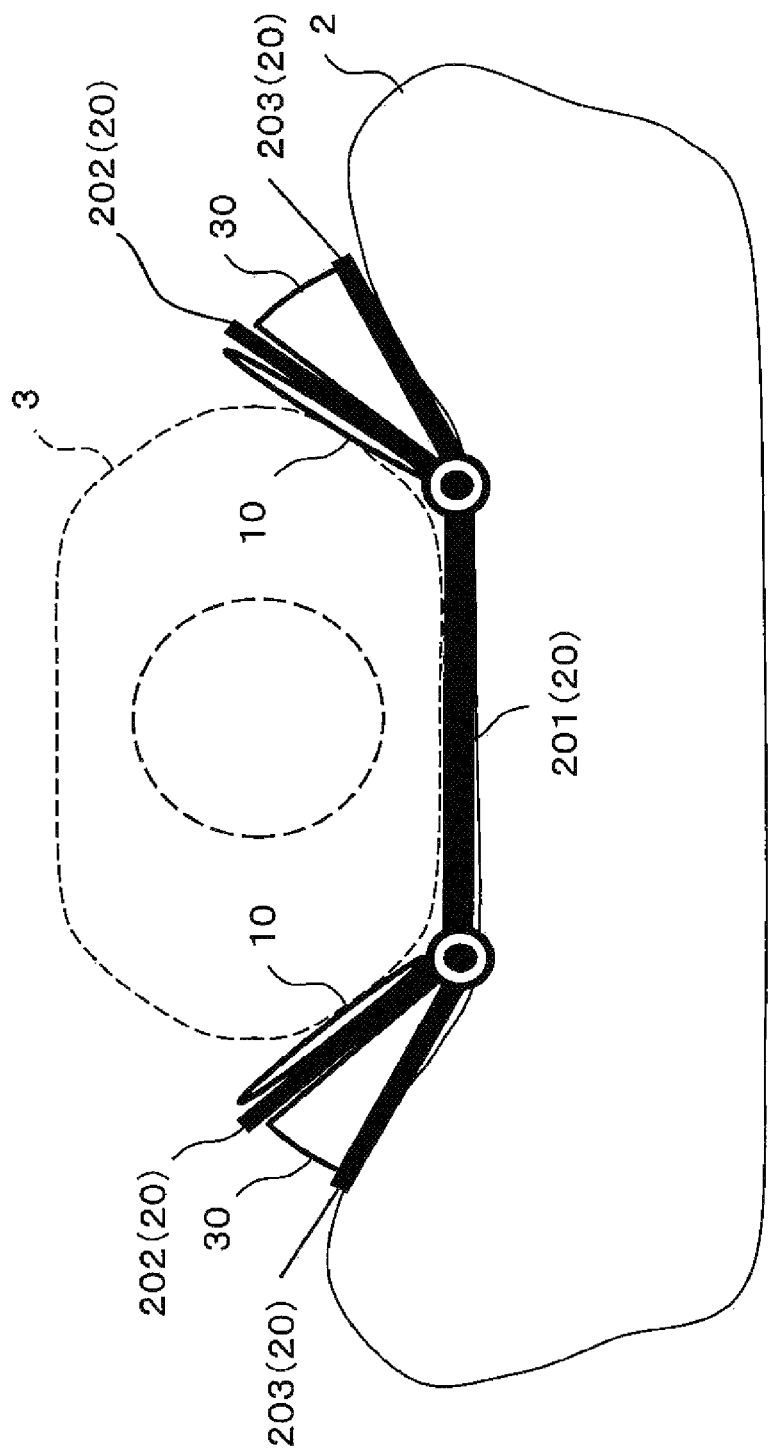
FIG. 10 is a plan view showing expansion of the adjustment portions in the massage device of FIG. 9.

As shown in FIG. 10, the adjustment portions 30 first expand so that the second supports 202 pivot toward the seat occupant 3. When the pressing portions 10 contact the seat occupant 3, the adjustment portions 30 stop expanding and the second supports 202 stop pivoting.

Figure 11:
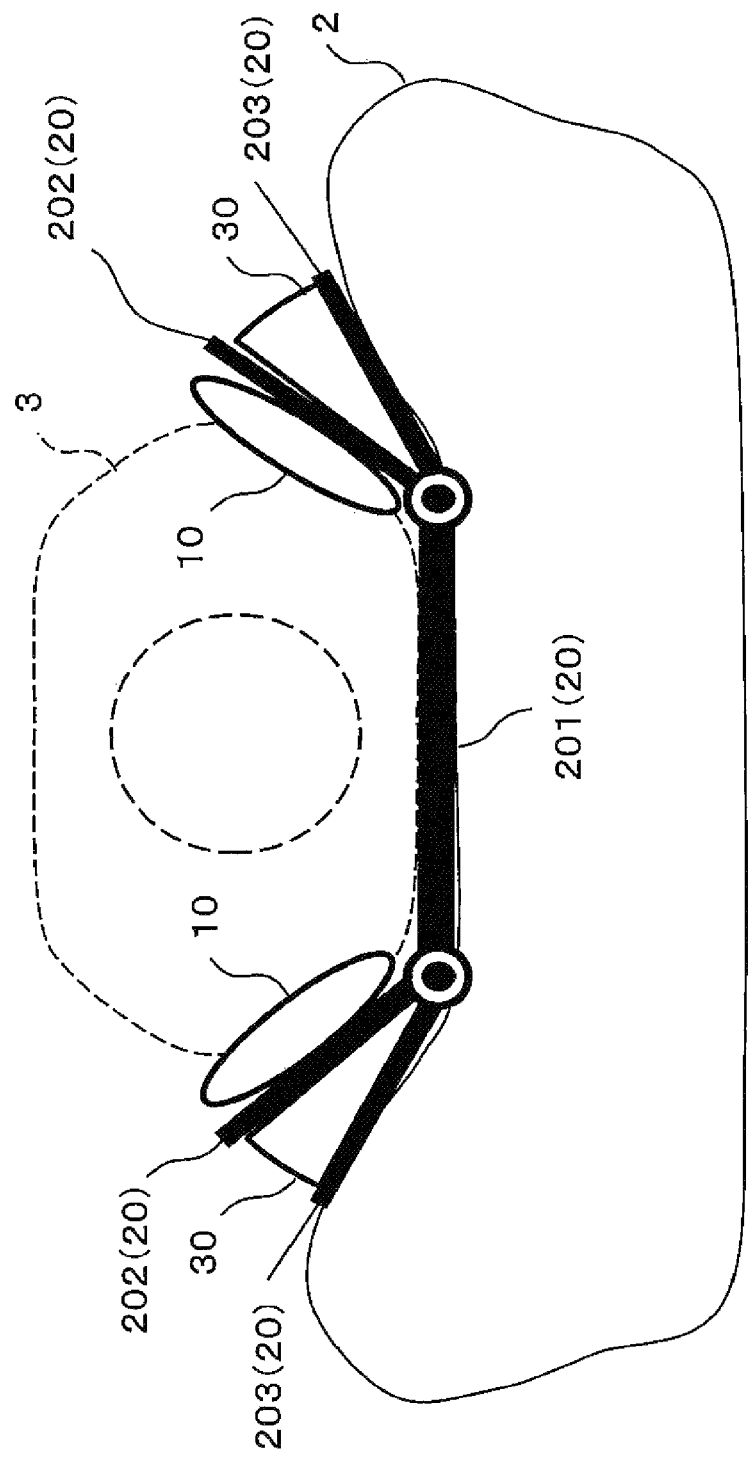
FIG. 11 is a plan view showing expansion of the pressing portions in the massage device of FIG. 10.
Figure 12:
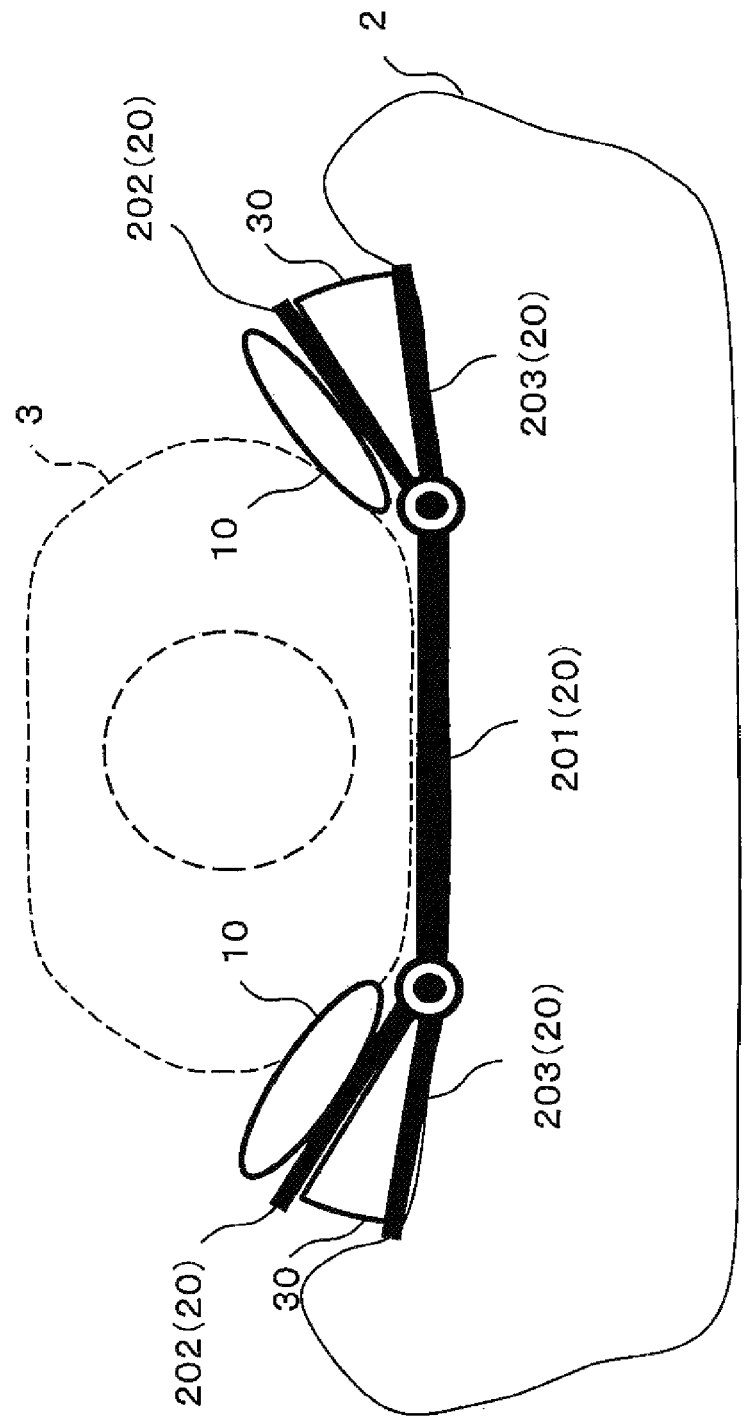
FIG. 12 is a plan view showing deformation of the seat by the massage device of FIG. 11.
Figure 13:
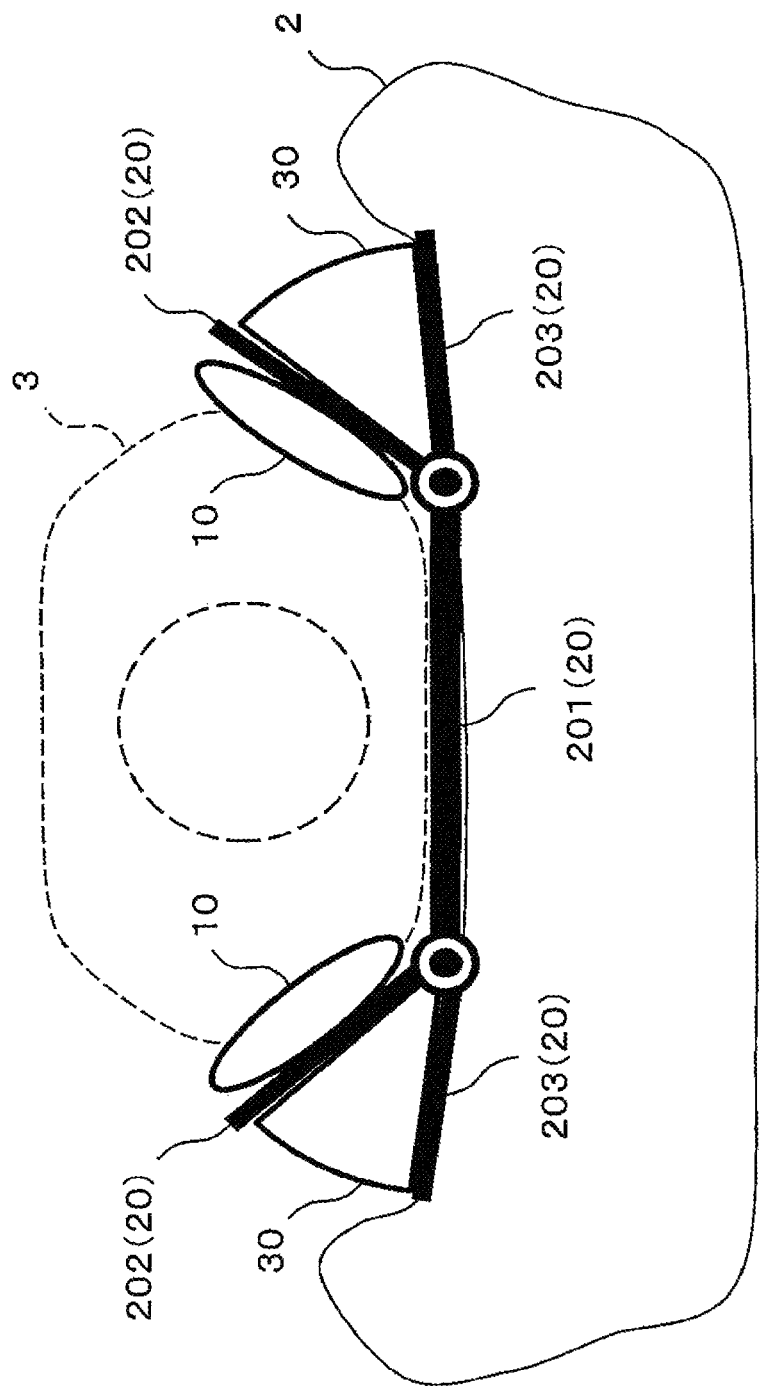
FIG. 13 is a plan view showing expansion of the adjustment portions in accordance with the deformation of the seat of FIG. 12.

Next, as shown in FIG. 11, the pressing portions 10 expand to press the seat occupant 3. In this state, as shown in FIG. 12, the third supports 203 press the seat 2 with reactions acting on actions of the pressing portions 10 that press the seat occupant 3. As a result, the second supports 202, the third supports 203, and the adjustment portions 30 pivot toward the seat 2, thereby recessing and deforming the seat 2. When such deformation occurs, as shown in FIG. 13, the adjustment portions 30 start expanding and the second supports 202 pivot toward the seat occupant 3. When the angles formed by the second supports 202 and the first support 201 return to the positions prior to the expansion of the pressing portions 10, the adjustment portions 30 stop expanding.

When the inner pressure of the pressing portions 10 reach the threshold value, the pressing portions 10 stop expanding. When the predetermined time has elapsed since the pressing portion 10 stopped expanding, the pressing portions 10 contract.

Thereafter, the massage device 1 repeatedly expands and contracts the pressing portions 10 until the elapse of a certain time since receiving a signal from the operation portion 71. In this manner, the massage device 1 massages the seat occupant 3.

The above-described embodiment has the following advantages.

(1) When expansion of the pressing portion 10 deforms the seat 2, the controller 70 can drive the adjustment portion 30 such that the pressing portion 10 moves toward the seat occupant 3. This limits the attenuation of a force of the pressing portion 10 that presses the seat occupant 3.

(2) The massage device 1 is separate from the seat 2. Thus, the massage device 1 can be arranged on any seat 2. Thus, the massage device 1, which limits the attenuation of a force of the pressing portion 10 that presses the seat occupant 3, is applicable to any seat 2.

(3) When expansion of the pressing portion 10 deforms the seat 2, the second support 202 pivots toward the seat 2, that is, the supported part of the pressing portion 10 moves toward the seat 2. Thus, even if the massage device 1 and the seat 2 are separate from each other, the angle detector 80 can detect the deformation of the seat 2 by detecting the angle formed by the first support 201 and the second support 202 (by detecting the position of the supported part of the pressing portion 10).

(4) In a case in which the detection result of the angle detector 80 becomes larger than the stored value V when the first switch valve 521 is open, the adjustment portion 30 is expanded until the detection result of the angle detector 80 becomes less than or equal to the stored value V. This allows the position of the second support 202 (i.e., the position of the supported part of the pressing portion 10) to return to the position prior to the expansion of the pressing portion 10. This further limits the attenuation of a force that presses the seat occupant 3.

(5) When the pressing portion 10 contacts the seat occupant 3 during driving of the adjustment portion 30, the inner pressure of the adjustment portion 30 increases more easily than before. This allows the controller 70 to determine a contact state between the pressing portion 10 and the seat occupant 3 from the gradient of the inner pressure of the adjustment portion 30 detected by the pressure detector 60. Thus, the controller 70 causes the adjustment portion 30 to expand until the gradient of the inner pressure of the adjustment portion 30 detected by the pressure detector 60 reaches the first threshold value, thereby causing the pressing portion 10 to press the seat occupant 3 with a proper force.

Modifications of the above-described embodiment will now be described.

The massage device 1 may be, for example, incorporated in the seat 2. In this case, even if deterioration of the seat 2 over time causes the seat 2 to deform easily, the adjustment portion 30 can be driven such that the pressing portion 10 properly contacts the seat occupant 3. Further, in this case, instead of the angle detector 80, a sensor that detects deformation of the seat 2 incorporated in the seat 2 (one example of a deformation detector) may be arranged. This sensor simply needs to be, for example, a movement sensor that detects movement in the front-rear direction of the surface of the seat 2.

Instead of the first pressure detector 601, a flow rate gauge may be used. For example, the flow rate gauge may be arranged at a position of the first passage 501 where the first pressure detector 601 is arranged to detect the amount of air supplied to the pressing portion 10 and the amount of air discharged from the pressing portion 10.

In a case in which the detection result of the angle detector 80 becomes small when the pressing portion 10 is being driven, a process of causing the adjustment portion 30 to contract may be performed. This reduces the pressing of the seat occupant 3 by the second support 202 regardless of whether the pressing portion 10 expands or contracts.

Other than during expansion of the pressing portion 10, the adjustment portion 30 may be driven in accordance with a change in the detection result of the angle detector 80. For example, other than during expansion of the pressing portion 10, when a change in the posture of the seat occupant 3 changes the detection result of the angle detector 80, the adjustment portion 30 may be driven. That is, after driving of the pressing portion 10 is initially started to perform a massaging process, the detection by the angle detector 80 and the driving of the adjustment portion 30 based on the detection result may be performed at any time.

The adjustment portion 30 does not have to perform the adjustment portion discharging process in step S6 of FIG. 3. This eliminates the need to expand the adjustment portion 30 when the seat occupant 3 performs massaging again. In this case, for example, when an end switch arranged on the operation portion 71 is operated, it is preferred that air in the adjustment portion 30 be discharged.

Figure 4:
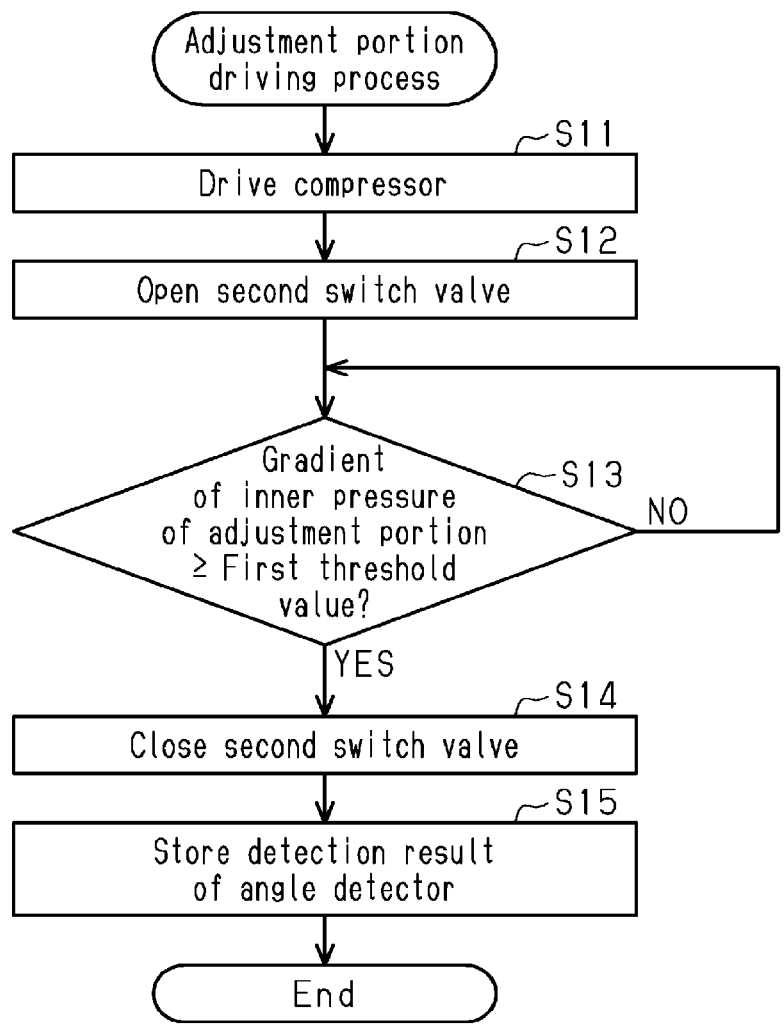
FIG. 4 is a flowchart of an adjustment portion driving process executed by the controller of the massage device shown in FIG. 2.

In the above-described embodiment, the determination of step S13 in FIG. 4 is performed based on the gradient of the inner pressure of the adjustment portion 30. Instead, the determination may be performed based on the value of the inner pressure of the adjustment portion 30. In this case, it is preferred that the first threshold value be set in advance in accordance with, for example, the volume of the adjustment portion 30 and the amount of air discharged by the compressor 40.

Alternatively, the determination of step S13 in FIG. 4 may be performed based on a change amount per unit of time of the angle formed by the second support 202 and the first support 201. For example, a threshold value simply needs to be set between a change amount per unit of time of the angle formed by the second support 202 and the first support 201 until the pressing portion 10 contacts the seat occupant 3 and a change amount per unit of time of the angle formed by the second support 202 and the first support 201 after the pressing portion 10 contacts the seat occupant 3. In this case, even if the second pressure detector 602 is not provided, the contact of the pressing portion 10 with the seat occupant 3 can be detected.

The second threshold value may be a fixed value or may be continuously or gradually variable. When the second threshold value is variable, it is preferred that the second threshold value be switched by a switch arranged on the operation portion 71. This allows the seat occupant 3 to change how strongly the pressing portion 10 presses the seat occupant 3.

The process performed in step S5 in FIG. 3 may be set as the same as the process performed in step S2 in FIG. 3. This limits the attenuation of a force of the pressing portion 10 that presses the seat occupant 3 even if the pressing portion 10 repeatedly expands and contracts to increase the deformation amount of the seat 2.

The massage device 1 may be arranged on the seating surface of the seat 2. In this case, the pressing portions 10 massage, for example, the sides of the thighs of the seat occupant 3.

The adjustment portions 30 do not have to be elastic bag-shaped members. For example, the adjustment portions 30 may be actuators that pivot the second supports 202.

The supports 20 do not have to be arranged. For example, the pressing portions 10 and the adjustment portions 30 may be coupled to each other in series in the front-rear direction of the seat 2.

The second supports 202 and the third supports 203 do not have to be coupled to each other pivotally relative to the first support 201 and simply need to be movable relative to the first support 201. In this case, the angle detector 80 simply needs to be replaced with a sensor that detects movement of the second supports 202 relative to the first support 201, that is, movement of the position of the supported parts of the pressing portions 10 relative to the first support 201.

The angle detector 80 may be arranged on each of the opposite sides of the first support 201, that is, the coupled part of the first support 201 and each second support 202. This allows deformation of the seat 2 to be detected more accurately.

The first switch valve 521 may be arranged at two portions of the first passage 501 that branch and extend toward the two pressing portions 10. This allows the two pressing portions 10 to expand and contract independently from each other. Further, the second switch valve 522 may be arranged at two portions of the second passage 502 that branch and extend toward the two adjustment portions 30. This allows the two adjustment portions 30 to expand and contract independently from each other.

The controller 70 is not limited to one that performs software processing on all processes executed by itself. For example, the controller 70 may include a dedicated hardware circuit (for example, application specific integrated circuit: ASIC) that executes hardware processing on at least part of the processes executed by itself. That is, the controller 70 may be circuitry including: 1) one or more processors that operate according to a computer program (software); 2) one or more dedicated hardware circuits that execute at least part of various processes, or 3) a combination thereof. The processor includes a CPU and memories such as a RAM and a ROM. The memories store program codes or commands configured to cause the CPU to execute processes. The memories, or computer readable media, include any type of media that are accessible by general-purpose computers and dedicated computers.

The invention claimed is:

1. A massage device for a seat, the massage device comprising:
a pressing portion configured to expand to press a seat occupant seated on the seat;
an adjustment portion configured to adjust a position of the pressing portion between the seat occupant and the seat;
a deformation detector configured to detect deformation of the seat caused by expansion of the pressing portion; and
a controller configured to control the adjustment portion based on a detection result of the deformation detector.

2. The massage device according to claim 1, wherein the massage device is separate from the seat.

3. The massage device according to claim 2, wherein
the adjustment portion is located between the pressing portion and the seat,
the pressing portion includes a supported part supported by the adjustment portion, and
the deformation detector is configured to detect a position of the supported part of the pressing portion.

4. The massage device according to claim 3, wherein
the controller is configured to drive the pressing portion, and
the controller is configured to, after starting driving the pressing portion, drive the adjustment portion such that the position of the supported part of the pressing portion returns to a position prior to the driving of the pressing portion.

5. The massage device according to claim 3, wherein the controller is configured to, when determining that the position of the supported part of the pressing portion has been moved during driving of the pressing portion, drive the adjustment portion such that the position of the supported part of the pressing portion returns to a position prior to the driving of the pressing portion.

6. The massage device according to claim 1, wherein
the pressing portion includes a supported part supported by the adjustment portion, and
the deformation detector is configured to detect a position of the supported part of the pressing portion.

7. The massage device according to claim 6, wherein
the controller is configured to drive the pressing portion, and
the controller is configured to, after starting driving the pressing portion, drive the adjustment portion such that the position of the supported part of the pressing portion returns to a position prior to the driving of the pressing portion.

8. The massage device according to claim 6, wherein the controller is configured to, when determining that the position of the supported part of the pressing portion has been moved during driving of the pressing portion, drive the adjustment portion such that the position of the supported part of the pressing portion returns to a position prior to the driving of the pressing portion.

9. The massage device according to claim 1, wherein
the adjustment portion is configured to expand to adjust the position of the pressing portion,
the massage device further comprises a pressure detector configured to detect an inner pressure of the adjustment portion, and
the controller is configured to drive the adjustment portion based on a change amount per unit of time of the inner pressure of the adjustment portion.

10. A massage device for a seat, the massage device comprising:
a first airbag configured to expand to press a seat occupant seated on the seat;
a second airbag configured to adjust a position of the first airbag between the seat occupant and the seat;
an angle sensor configured to detect deformation of the seat caused by expansion of the first airbag; and
a controller configured to control the second airbag based on a detection result of the angle sensor.

11. The massage device according to claim 10, wherein the massage device is separate from the seat.

12. The massage device according to claim 11, wherein
the second airbag is located between the first airbag and the seat,
the first airbag includes a supported part supported by the second airbag, and
the angle sensor is configured to detect a position of the supported part of the first airbag.

13. The massage device according to claim 12, wherein
the controller is configured to drive the first airbag, and
the controller is configured to, after starting driving the first airbag, drive the second airbag such that the position of the supported part of the first airbag returns to a position prior to the driving of the first airbag.

14. The massage device according to claim 12, wherein the controller is configured to, when determining that the position of the supported part of the first airbag has been moved during driving of the first airbag, drive the second airbag such that the position of the supported part of the first airbag returns to a position prior to the driving of the first airbag.

15. The massage device according to claim 10, wherein
the first airbag includes a supported part supported by the second airbag, and
the angle sensor is configured to detect a position of the supported part of the first airbag.

16. The massage device according to claim 15, wherein
the controller is configured to drive the first airbag, and
the controller is configured to, after starting driving the first airbag, drive the second airbag such that the position of the supported part of the first airbag returns to a position prior to the driving of the first airbag.

17. The massage device according to claim 15, wherein the controller is configured to, when determining that the position of the supported part of the first airbag has been moved during driving of the first airbag, drive the second airbag such that the position of the supported part of the first airbag returns to a position prior to the driving of the first airbag.

18. The massage device according to claim 10, wherein
the second airbag is configured to expand to adjust the position of the first airbag,
the massage device further comprises a pressure detector configured to detect an inner pressure of the second airbag, and the controller is configured to drive the second airbag based on a change amount per unit of time of the inner pressure of the second airbag.

\* \* \* \* \*